(12) United States Patent
Dromard et al.

(10) Patent No.: US 7,799,304 B2
(45) Date of Patent: Sep. 21, 2010

(54) HIGHLY-STRUCTURED SILICA HAVING A LOW WATER UPTAKE, PREPARATION METHOD THEREOF AND USES OF SAME

(75) Inventors: Adrien Dromard, Lyons (FR); Yvonick Chevallier, Saint-Romain-Au-Mont d'Or (FR); Rémi Valero, Saint Jean de Thurigneux (FR); Dominique Petit, Saint-Cyr-Au-Mont-d'Or (FR)

(73) Assignee: Rhodia Chimie, Aubervilliers (FR)

( * ) Notice: Subject to any disclaimer, the term of this patent is extended or adjusted under 35 U.S.C. 154(b) by 501 days.

(21) Appl. No.: 10/583,417

(22) PCT Filed: Dec. 20, 2004

(86) PCT No.: PCT/FR2004/003313

§ 371 (c)(1),
(2), (4) Date: Apr. 26, 2007

(87) PCT Pub. No.: WO2005/061384

PCT Pub. Date: Jul. 7, 2005

(65) Prior Publication Data

US 2008/0019898 A1    Jan. 24, 2008

(30) Foreign Application Priority Data

Dec. 19, 2003 (FR) ................................. 03 15063
Apr. 8, 2004 (FR) ................................. 04 03700

(51) Int. Cl.
*C01B 33/12* (2006.01)
(52) U.S. Cl. ........................................ 423/339; 423/335
(58) Field of Classification Search ................ 423/335, 423/339
See application file for complete search history.

(56) References Cited

U.S. PATENT DOCUMENTS

| 5,968,470 A | 10/1999 | Persello |
| 6,001,322 A | 12/1999 | Chevallier et al. |
| 6,335,396 B1 | 1/2002 | Chevallier et al. |
| 7,033,576 B2 * | 4/2006 | Chevallier et al. ............ 424/49 |
| 2005/0074386 A1 * | 4/2005 | Valero et al. ................ 423/338 |

FOREIGN PATENT DOCUMENTS

| EP | 0 407 262 A1 | 1/1991 |
| WO | WO 95/09127 | 4/1995 |
| WO | WO 95/09128 | 4/1995 |
| WO | WO 0193803 A2 * | 12/2001 |
| WO | WO 03055801 A1 * | 7/2003 |

OTHER PUBLICATIONS

S. Brunauer et al., "Adsorption of Gases in Multimolecular Layers", *J. Chem.* Soc, vol. 60, Feb. 1938, pp. 309-319.

* cited by examiner

*Primary Examiner*—Timothy C Vanoy
*Assistant Examiner*—Richard M Rump
(74) *Attorney, Agent, or Firm*—Buchanan Ingersoll & Rooney PC

(57) ABSTRACT

The invention relates to a highly-structured precipitated silica having a low water uptake and high dispersibility in different pasty or solid matrices or media, elastomers or silicon, and to the preparation method thereof. The invention also relates to the use of said silica, for example, as a reinforcing filler in matrices based on elastomers (clear or semi-clear for shoe soles), in silicon matrices (in particular, for the coating of electric cables), as a filler and/or support and/or vehicle in different compositions (food compositions, cosmetic compositions, pharmaceutical compositions, compositions for the production of paints or paper, compositions for the production of porous membrane separators for batteries) or as a thickening agent in toothpastes.

30 Claims, No Drawings

HIGHLY-STRUCTURED SILICA HAVING A LOW WATER UPTAKE, PREPARATION METHOD THEREOF AND USES OF SAME

This application is an application under 35 U.S.C. Section 371 of International Application Number PCT/FR2004/003313 filed on Dec. 20, 2004.

The present invention relates to a novel highly-structured precipitated silica having a low water uptake and to a process for the preparation of said silica.

It also relates to its use as reinforcing filler in matrices based on elastomers, in particular clear or semi-clear elastomers, for shoe soles or in silicon matrices, for example intended for the coating of electric cables.

It also relates to its use in particular as filler and/or carrier and/or excipient in various compositions, such as food, cosmetic or pharmaceutical compositions, compositions for the manufacture of paints or paper, or compositions intended for the manufacture of separating porous membranes for batteries (battery separators), or as thickener agent in dentifrice formulations.

"Precipitated" silicas often exhibit a high affinity for water due in particular to the presence at their surface of water-greedy Si—OH groups. The commonest precipitated silicas generally exhibit water uptakes (according to the test defined below) of greater than 7%, generally of the order of 8 to 10%.

A process for preparing a precipitated silica having a low water uptake (of the order of 4 to 6%) forms the subject matter of application WO 03/055801; the silica then obtained generally exhibits a CTAB specific surface (external surface) of 100 to 200 m$^2$/g and a DOP oil uptake of 150 to 300 ml/100 g; it is indicated that this silica can be used for the reinforcing of silicone-based elastomeric matrices, in particular room temperature or high temperature vulcanizable silicone matrices, or of transparent or translucent elastomeric matrices for shoe soles; it is also mentioned that this silica can also be used as thickening agent in organic or aqueous media, in particular toothpastes.

Highly structured precipitated silicas exhibiting a DOP oil uptake of greater than 250 ml/100 g, in particular of the order of 300 to 320 ml/100 g, and a CTAB specific surface (external surface) of 70 to 250 m$^2$/g have already been provided as thickening or texturing agent in dentifrice compositions (application WO 01/93803); such silicas exhibit a water uptake of greater than 7%, that is to say conventional for precipitated silicas.

The Applicant has now found a novel precipitated silica which exhibits good dispersing performances in formulation and which advantageously exhibits a high dispersibility in various solid, in particular elastomeric (clear, semi-clear, silicone), or pasty matrices or media, and in even a high light transmission. This is reflected in particular by a good reinforcing and/or thickening power. This silica is particularly suitable for being employed especially as reinforcing filler in matrices based on elastomers, for example clear or semi-clear elastomers, for shoe soles or in silicone matrices, for example room temperature or high temperature vulcanizable silicone matrices. A particularly advantageous application of this silica consists, inter alia, of its use as thickening agent in dentifrices formulations.

A first subject matter of the invention consists of a precipitated silica exhibiting:
- a CTAB specific surface of 140 to 230 m$^2$/g, preferably of 145 to 195 m$^2$/g, more preferably of 145 to 185 m$^2$/g, very particularly of 150 to 185 m$^2$/g, in particular of 150 to 180 m$^2$/g, for example of 155 to 175 m$^2$/g or of 160 to 180 m$^2$/g,
- a DOP oil uptake of greater than 300 ml/100 g, preferably of greater than 310 ml/100 g, more preferably of 315 to 450 ml/100 g, very particularly of 320 to 400 ml/100 g, in particular of 340 to 380 ml/100 g,
- a water uptake of less than 6% and preferably of greater than 3%, very particularly of greater than or equal to 4% and of less than or equal to 5.8%,
- a pH of 3.5 to 7.5, preferably of 4 to 7, very particularly of 4 to 6,
- a level of residual anion, expressed as sodium sulfate, of less than or equal to 2%, preferably of less than or equal to 1.5%, particularly of less than or equal to 1% and very particularly of less than or equal to 0.5%,
- a mean particle size or a median particle diameter of less than 30 μm or of between 30 μm and 20 mm.

According to a first alternative form of the invention, the silica exhibits a mean particle size or a median particle diameter of less than 30 μm, preferably of less than 20 μm, in particular of between 5 and 15 μm, especially between 8 and 13 μm.

According to a second alternative form of the invention, the silica exhibits a mean particle size or a median particle diameter of between 30 μm and 20 mm.

The silica according to this second alternative form of the invention very preferably exhibits a CTAB specific surface of 145 to 185 m$^2$/g, in particular of 150 to 180 m$^2$/g, very particularly of 155 to 175 m$^2$/g.

The CTAB specific surface is the external surface determined according to standard NFT 45-007 (November 1987).

The DOP oil uptake is determined according to standard ISO 787/5, dioctyl phthalate being employed.

The affinity of a silica with regard to water, expressed by its "water uptake" characteristic, reflects the more or less marked tendency which water molecules exhibit of being adsorbed on the surface of silica.

The principle of the test for measuring this characteristic consists in placing the predried sample of silica under given relative humidity conditions for a predefined period of time; the silica hydrates, which causes the weight of the sample to change from a starting value w (in the dried state) to a final value (w+dw). "Water uptake" of a silica will specifically denote the dw/w ratio, expressed as percentage, calculated for a silica sample subjected to the following conditions during the test:
- preliminary drying: 8 hours at 105° C.;
- hydration: 24 hours at 20° C. under a relative humidity of 70%.

The experimental protocol employed consists in:
- exactly weighing approximately 2 g of the test silica;
- drying the silica thus weighed for 8 hours in an oven adjusted to a temperature of 105° C.;
- determining the weight w of the dried silica obtained on conclusion of the drying operation;
- placing the dried silica obtained in a closed container (for example in a desiccator) containing a water/glycerol mixture with a water/glycerol ratio by weight of 35/65, so that the relative humidity of the closed medium is 70%, for 24 hours at 20° C.;
- determining the weight (w+dw) or the silica obtained subsequent to this treatment for 24 hours at 70% relative humidity, this weight being measured immediately after having removed the silica from the desiccator, so as to avoid a variation in the weight of the silica under the influence of the change in hygrometry between the medium at 70% relative humidity and the atmosphere of the laboratory.

The pH of the silica is measured according to standard ISO 787/9 (pH of a 5% by weight suspension of silica in deionized water).

The silica according to the invention can be provided in the form of beads, of granules (or other aggregates) or, preferably, of a powder having a mean particle size or a median particle diameter of at most 20 mm.

The silica according to the first alternative form of the invention can be provided in the form of beads, of granules (or other aggregates) or, preferably, of a powder having a mean particle size or a median particle diameter of less than 30 µm, preferably of less than 20 µm, in particular of between 5 and 15 µm, especially between 8 and 13 µm. This silica is particularly suitable for being employed as reinforcing filler in matrices based on elastomer(s), in particular clear or semi-clear elastomer(s), for shoe soles or as reinforcing filler in matrices based on silicone(s).

The silica according to the second alternative form of the invention can be provided in the form of beads, of granules (or other aggregates) or, preferably, of powder having a mean particle size or a median particle diameter of between 30 µm and 20 mm. It can in particular be a powder exhibiting a median particle diameter of at least 30 µm, preferably of at least 50 µm, and of less than 350 µm, preferably of less than 180 µm; this silica is particularly suitable for being used as thickening or texturing agent in dentifrice compositions or as reinforcing filler in matrices based on silicone(s).

The silica can also concern granules (or other aggregates) exhibiting a mean particle size of between 2 and 20 mm.

The mean size of the silica particles can be determined according to standard NF X 11507 (December 1970) by dry sieving and determining the diameter corresponding to a cumulative oversize of 50%.

The median diameter of the silica particles can be determined by laser diffraction according to standard NF X 11-666. The particle sizer used is of the Malvern Mastersizer type.

Measurement Criteria
optical concentration: 12±2%
measurement liquid: degassed demineralized water
absence of ultrasound
absence of dispersant
duration of the measurement: 10 seconds The precipitated silica according to the invention generally exhibits a median diameter d50 of the particles, after deagglomeration under ultrasound, of at most 35 µm, preferably of at most 30 µm, very particularly of at most 25 µm, in particular of at most 15 µm, for example of at most 10 µm.

The median diameter d50 of the silica after deagglomeration under ultrasound is measured using the Malvern Mastersizer particle sizer according to the following test:

The power of the ultrasound in the Malvern Mastersizer particle sizer being adjusted to the maximum graduation of 20, an amount of silica is introduced so as to obtain an optical concentration of 12±2%.

The median diameter d50 and the percentage of silica particles with a diameter of greater than 51 µm are measured after having kept the vessel subjected to ultrasound for 60 seconds, the vessel being homogenized by circulation of the suspension using a centrifugal pump. The measurement is recorded 10 seconds after ceasing to apply ultrasound.

The ability of the silica according to the invention to disperse or to deagglomerate can also be assessed by a particle size measurement (by laser diffraction) carried out on a suspension of silica deagglomerated beforehand by ultrasonication (splitting of the objects from 0.1 to a few tens of microns). The deagglomeration under ultrasound is carried out using a Vibracell Bioblock (600 W) ultrasound generator equipped with a probe with a diameter of 19 mm. The particle size measurement is carried out by laser diffraction on a Sympatec particle sizer.

2 grams of silica are weighed out into a sample tube (height: 6 cm and diameter: 4 cm) and are made up to 50 grams by addition of deionized water: a 4% aqueous silica suspension is thus produced and is homogenized for 2 minutes with magnetic stirring. Deagglomeration is subsequently carried out under ultrasound as follows: the probe being immersed over a length of 4 cm, the output power is adjusted so as to obtain a deviation of the needle of the power dial indicating 20%. Deagglomeration is carried out for 420 seconds. The particle size measurement is subsequently carried out by introducing, into the vessel or the particle sizer, a volume V (expressed in ml) of the homogenized suspension necessary in order to obtain an optical density of the order of 20.

A deagglomeration factor $F_D$ is then given by the equation:

$F_D = 10 \times V$/optical density of the suspension measured by the particle sizer (this optical density is of the order of 20).

This deagglomeration factor $F_D$ is indicative of the level of particles with a size of less than 0.1 µm which are not detected by the particle sizer. This factor increases as the silica exhibits an increased aptitude for deagglomeration.

The value of the median diameter d50 which is obtained according to this test decreases as the silica exhibits an increased aptitude for deagglomeration.

Preferably, the silica according to the invention has a median diameter d50, after deagglomeration under ultrasound, of less than 6 µm, in particular of less than 5 µm, for example of less than 3.5 µm.

The silica according to the invention generally exhibits an ultrasound deagglomeration factor $F_D$ of greater than 5.5 ml, in particular greater than 7.5 ml, for example greater than 11.5 ml.

The silicas according to the invention preferably exhibit a BET specific surface such that the BET-CTAB difference is at most 30 m$^2$/g, preferably at most 25 m$^2$/g, more preferably at most 20 m$^2$/g, in particular at most 10 m$^2$/g.

The BET specific surface is determined according to the Brunauer-Emmett-Teller method described in the Journal of the American Chemical Society, vol. 60, page 309, February 1938, corresponding to standard NFT 45007 (November 1987).

Furthermore, the silicas according to the invention generally exhibit a packing density, measured according to standard ISO 787/11, of at most 0.3 g/ml, preferably of 0.04 to 0.3 g/ml, more preferably of 0.05 to 0.3 g/ml, in particular of 0.05 to 0.2 g/ml; this packing density can also be between 0.1 and 0.3 g/ml, in particular between 0.1 and 0.27 g/ml, especially between 0.15 and 20.25 g/ml.

The loss on ignition (LOI) of the silica of the invention, measured according to standard ISO 3262/11, after treatment at 1000° C., is generally such that the difference between the LOI and the water content is less than 3.2%, preferably less than 3%, very particularly less than 2.7%.

The water content is the residual water content measured according to standard ISO 787/2, after heat treatment at 105° C. for 2 hours.

The water content of the silica according to the invention, in particular when it is intended to be used as filler in silica matrices, is generally less than 5%, preferably less than 4%, for example at most 3%, of the total weight of the sample.

The silica according to the invention can additionally exhibit a level of transmission of at least 70% at a refractive index in glycerol lying between 1.450 and 1.467.

The refractive index under consideration is that corresponding to the most transparent suspension (maximum transmission) of this silica in various water-glycerol solutions, which transparency is determined by the transmission at 589 nm with a spectrophotometer. Each suspension is obtained by dispersing 2 g of silica in 18 g of water/glycerol solution and then deaerating under a slight vacuum before reading the transmission (reading carried with the silica-free water/glycerol solution as reference product) on the spectrophotometer and the refractive index on a refractometer.

A second subject matter of the invention consists of a process for the preparation of the highly-structured silica having a low water uptake described above, comprising the following successive stages:

(a) producing a starting vessel heel with a temperature of between 80 and 100° C., preferably of greater than or equal to 90° C., comprising water and a silicate, the concentration of silicate in said vessel heel, expressed as $SiO_2$ equivalent, being less than or equal to 15 g/l;

(b) adding, at a temperature of between 80 and 100° C., preferably 90 and 100° C., an acidifying agent to bring the pH of the medium to a value of between 7 and 8, preferably to a value of between 7.2 and 7.8 and advantageously between 7.3 and 7.7 (typically to a value substantially equal to 7.5);

(c) in the medium thus produced, carrying out, at a temperature of between 80 and 100° C., preferably between 90 and 100° C., the simultaneous addition of a silicate and of an acidifying agent, the respective amounts of silicate and of acidifying agent added over time being specifically chosen so that, throughout the duration of the addition:

the pH of the reaction medium remains between 7 and 8 and advantageously between 7.2 and 7.8; and the concentration of silicon in the medium, expressed as $SiO_2$ equivalent, remains less than or equal to 35 g/l;

(d) adding, at a temperature of between 80 and 100° C., preferably between 90 and 100° C., an acidifying agent to the medium obtained on conclusion of stage (c) so as to bring the medium to a pH of between 3 and 6.5;

(e) filtering the aqueous silica dispersion obtained;

(f) drying the filtration cake produced on conclusion of the filtration, preferably washing it beforehand;

(g) optionally milling or micronizing the silica obtained on conclusion of stage (f), said process being characterized in that the filtration cake exhibits, prior to the drying of it in stage (f), a loss on ignition at 1000° C. of greater than 82%, preferably of at least 84%, very particularly of 84 to 88%.

The silicates employed in stages (a) and (c) of the process can be chosen from all the common forms of silicates. Advantageously, the silicates used according to the invention are alkali metal silicates, such as, for example, sodium or potassium silicates.

Particularly preferably, the silicate of stage (a) is a sodium silicate, as well as that added during stage (c). The sodium silicate employed is then generally characterized by an $SiO_2/Na_2O$ ratio by weight of between 2 and 4, advantageously between 3 and 3.6, this $SiO_2/Na_2O$ ratio by weight preferably being between 3.3 and 3.5 (typically, this ratio is substantially equal to 3.4).

The vessel heel of stage (a) of the process is generally provided in the form of an aqueous silicate solution, the concentration of which is characteristically less than or equal to 15 g/l. Typically, the concentration of silicate in the vessel heel of stage (a), expressed as $SiO_2$ equivalent, is between 1 and 15 g/l. This concentration of silicate in the vessel heel of stage (a), expressed as $SiO_2$ equivalent, is advantageously less than or equal to 10 g/l and preferably less than or equal to 9 g/l.

The vessel heel of stage (a) generally has a pH of the order of 9 to 13.

Stage (b) of the process of the invention consists specifically in reducing this value of the pH by addition of an acidifying agent, so as to bring the pH to the medium within the range from 7 to 8, where it has been demonstrated that the reaction for the precipitation of the silica takes place in optimum fashion. The term "acidifying agent" is understood to mean any inorganic or organic acidic compound capable of being able to lead to a reduction in the pH of the vessel heel. Thus, use may advantageously be made, as acidifying agent, of an inorganic acid, such as sulfuric acid, hydrochloric acid or nitric acid, or alternatively of an organic acid, such as acetic acid, formic acid or carbonic acid.

Advantageously, no electrolyte is added during the process, in particular in stage (a). The term of "electrolyte" is to be understood here as normally accepted, that is to say that it denotes any ionic or molecular substance which, when it is in solution, decomposes or dissociates to form ions or charged particles (the usual electrolytes are alkali metal and alkaline earth metal salts, in particular the salt of the starting silicate metal and of the acidifying agent, such as sodium chloride in the case of the reaction of a sodium silicate with hydrochloric acid or sodium sulfate in the case of the reaction of a sodium silicate with sulfuric acid).

The acidifying agent employed in stage (b) of the process is preferably sulfuric acid, in particular when the silicate present in the starting vessel heel is an alkali metal silicate. Generally, the acidifying agent of stage (b) is most often introduced in the form of an aqueous solution, preferably a dilute aqueous solution, generally with a normality of between 0.25 and 8N. Thus, in stage (b), the reduction in the pH of the medium can advantageously be carried out by addition of an aqueous sulfuric acid solution with a concentration of between 10 and 350 g/l and preferably between 50 and 250 g/l.

Whatever the exact nature of the acidifying agent of stage (b), this acidifying agent must be employed so that its addition results in the reduction in the pH of the medium down to a value of between 7 and 8. The amount of acidifying agent to be employed in this context is generally determined in practice by measuring the change in the pH during the addition, the addition of the acidifying agent of stage (b) being continued until the pH reaches the desired value.

Furthermore, the addition of stage (b) is preferably carried out gradually, that is to say advantageously, as a general rule, with an addition time of between 3 and 60 minutes, generally at least equal to 5 minutes and preferably at least equal to 10 minutes. However, this addition time is advantageously less than 30 minutes.

According to a specific embodiment which can be envisaged for stage (b), this stage can include a maturing process which, if appropriate, is carried out by leaving the medium to change for a period of time generally of between 5 and 30 minutes, preferably at a temperature of between 90 and 100° C., it being understood that, subsequent to this maturing, the pH of the reaction medium is adjusted if necessary, in particular by addition of an acidifying agent, so that, on conclusion of stage (b), the pH of the medium lies within the pH range between 7 and 8 and advantageously within the above-mentioned preferred ranges.

Subsequent to stage (b), by which the pH of the reaction medium is brought within the preferred region from 7 to 8 and preferably to approximately 7.5, stage (c) of the process consists in continuing the process for the precipitation of silica by introducing additional silicate and by specifically maintaining the pH of the medium within the region between 7 and 8, preferably at a substantially constant value, this constant value then preferably being close to 7.5, that is to say generally between 7.3 and 7.7.

To do this, the silicate of stage (c) is introduced in conjunction with an acidifying agent which opposes the increase in pH which would be observed by adding the silicate alone. Preferably, stage (c) of the process of the invention is carried out immediately after obtaining, for the medium, the desired pH in stage (b). The "simultaneous addition" of the silicate and of the acidifying agent which is carried out during stage (c) advantageously consists of a continuous addition of silicate to the medium, during which the pH of the medium is measured and during which the value of this pH is regulated by introduction of the acidifying agent, it being possible, for example, for this introduction of the acidifying agent to be carried out as soon as the pH of the medium becomes greater than a control value of between 7 and 8, this control value generally being set in a vicinity of 7.5. By this means, success is achieved in maintaining, in the medium, a substantial constant value of the pH, that is to say advantageously varying to +/−0.2 pH unit (preferably to +/−0.1 pH unit) around a set value, generally of between 7.3 and 7.7.

Alternatively, the simultaneous addition of stage (c) can also consist of a continuous addition of acidifying agent to the medium, the pH then being regulated during the addition by introduction of the silicate, it being possible here again for this introduction with the silicates to be, for example, carried out as soon as the pH of the medium becomes less than a control value of between 7 and 8 generally fixed in the vicinity of 7.5. By this means, success is also achieved in keeping the medium at a substantially constant pH, that is to say advantageously varying to +/−0.2 pH unit (preferably to +/−0.1 pH unit) around a set value generally between 7.3 and 7.7.

According to yet another embodiment which can be envisaged, the simultaneous addition of stage (c) can also consist of a continuous addition both of acidifying agent and of silicate with concentrations and flow rates calculated so that, throughout the duration of the addition, the pH of the medium remains between 7 and 8 and preferably between 7.2 and 7.8. In this case, the pH of the medium generally has a tendency to change during stage (c) or remaining within the abovementioned range but it can, in some cases, remain substantially equal to a constant value advantageously of the order of 7.5. In this context, it is generally preferable for, throughout stage (c), the instantaneous flow rates corresponding to the amount of silicate functional groups (expressed as molar equivalent of NaOH) introduced per second (recorded as $d_S$) and the amount of acid functional groups (as moles) introduced per second (recorded as $d_A$) to be such that the ratio $d_S/d_A$ remains continuously between 1.01 and 1.09 and preferably between 1.02 and 1.07.

Whatever the exact embodiment of stage (c), the silicate and the acidifying agent used are generally identical to those employed in stages (a) and (b). Thus, the silicate of stage (c) is preferably an alkali metal silicate, advantageously a sodium silicate, and the acidifying agent is preferably a strong inorganic acid, generally sulfuric acid.

Insofar as, during the simultaneous addition of stage (c), the concentration of silicon in the medium (expressed as $SiO_2$ equivalent) characteristically has to be kept below or equal to 35 g/l, the silicate introduced into the reaction medium during stage (c) is generally in the form of a dilute aqueous solution, that is to say with a concentration, expressed as $SiO_2$ equivalent, advantageously of between 10 and 360 g/l, preferably of less than 300 g/l and advantageously of less than 270 g/l, this being very particularly the case when alkali metal silicates, such as sodium silicates, are used. In the same way, the acidifying agent is generally in the form of a dilute aqueous solution which generally has a normality of between 0.25 and 8N and preferably between 0.5 and 4N. Thus, in the specific case of the use of an aqueous sulfuric acid solution as acidifying agent of stage (c), for example, the concentration of the solution is advantageously between 25 and 380 g/l and preferably between 50 and 300 g/l.

It should be emphasized that, in view of the use of dilute concentrations in the medium for the precipitation of the silicas, the concentrations of salts in this medium, in particular related to the reaction of the silicate and of the acidifying agent, are characteristically extremely low, which is reflected by a weak ionic strength within the precipitation medium employed.

Without wishing to be committed in any way to a specific theory, it appears possible to hypothesize that the control of the pH and of the concentrations employed makes it possible to minimize the formation of surface SiOH groups.

So as to further improve the control of the formation of the silica, it is particularly advantageous to carry out the simultaneous addition of stage (c) with silicate and acidifying agent flow rates which are relatively low, that is to say generally with an addition time of stage (c) preferably of between 15 and 300 minutes and preferably between 30 and 100 minutes. This is because such addition times generally result in the production of silicon particles exhibiting extremely low levels of surface Si—OH groups.

Generally, stage (c) of the process of the invention is carried out with stirring at a temperature of between 80 and 100° C. and generally at the same temperature as the addition of stage (b). Thus, the operating temperature of stage (c) can advantageously be between 90 and 100° C. and it is preferably of the order of 95° C. According to a specific alternative form of the process, this applying in particular with regard to the preparation of silicas which can be used in applications other than food, dentifrice, cosmetic or pharmaceutical applications, it is possible to introduce, into the reaction medium, during stage (c), preferably at the end of the stage (that is to say, typically during the period corresponding to the final quarter of this stage, generally during the final 5 to 15 minutes of this stage), an aluminum-based compound, preferably a salt of acidic nature, such as an aluminum sulfate, or alternatively a compound of basic nature, such as a sodium aluminate. The amount of aluminum compound introduced in this context is generally such that, within the reaction medium, the $Al/SiO_2$ ratio is between 0.1 and 1% by weight, this ratio preferably being at most equal to 0.6% and preferably less than or equal to 0.5%.

Whatever the exact embodiment of stage (c), the reaction medium is, on conclusion of this stage, specifically at a pH of between 7 and 8 and preferably of the order of 7.5.

Depending on the applications envisaged for the silica, stage (d) of acidification of the medium in the pH region from 3 to 6.5 can be varied by the amount of acidifying agent added. Preferably, the pH of the medium reached on conclusion of stage (d) is between 3.2 and 5.5.

The acidifying agent of stage (d) can without distinction be identical to or different from that or those employed in stages (b) and (c). Preferably, this acidifying agent of stage (d) is introduced into the medium in the form of an aqueous solution with a normality of between 0.25 and 8N. Advantageously, it is an aqueous sulfuric acid solution generally at a concentration of between 25 and 380 g/l, if appropriate.

The combined stages (a), (b), (c) and (d) of the process are preferably carried out at a temperature of between 90 and 100° C., advantageously at a temperature of between 93 and 97° C. and more advantageously still at a temperature substantially equal to 95° C. throughout the process.

According to an advantageous alternative form of the process of the invention, the aqueous silica dispersions obtained on conclusion of stages (c) and (d) can be subjected to a maturing stage generally carried out, if appropriate, by leaving the medium, preferably with stirring, at a temperature of between 90 and 100° C. for a period of time which can advantageously be between 15 and 240 minutes and preferably for a period of time of greater than 30 minutes, the temperature during the maturing preferably being substantially constant (if appropriate, advantageously substantially equal to 95° C.) or else increasing (generally stepwise, if appropriate) within the temperature range extending from 90 to 100° C.

It should be emphasized that the addition of an aluminum compound, in particular of aluminum sulfate type, which can be envisaged at the end of stage (c) can also be carried out during stage (d) or alternatively during the subsequent maturing stage, when this stage is carried out. Thus, generally, this addition of an aluminum-based compound to the medium can take place between stage (c) and stage (e).

Stages (e) and (f) of the process consist overall in recovering a silica in the solid form from the dispersion obtained on conclusion of the preceding stages.

Generally, during this stage (e), the dispersion obtained on conclusion of stage (d) and of the optional subsequent maturing stage is filtered through a filter press or is filtered under vacuum using a rotary filter, a belt filter or a flat filter, this filtration resulting in a "silica cake" being obtained. The silica cake obtained is then generally subjected to a washing stage, generally washing with water, preferably with a sufficiently long duration, so as to reduce its content of salts, and it is subsequently subjected in stage (f) to drying, in particular by a suitable atomization, for example using a rotary, nozzle, liquid pressure or two-fluid atomizer.

In this context, the silica cake is generally disintegrated beforehand, so as to form a silica slurry with a viscosity sufficiently low to provide for the pumping thereof to the atomizer.

According to the invention, this slurry exhibits a loss on ignition at 1000° C. of greater than 82% by weight, preferably of at least 84% by weight, more particularly of 84 to 88% by weight.

If appropriate, the disintegrating operation can, for example, be carried out in a known way by subjecting the cake to a mechanical action and optionally to a chemical action (addition of an acid or of an aluminum-based compound).

Generally, the slurry of low viscosity resulting from such a disintegration operation is provided in the form of an aqueous silica dispersion which can be directly pumped to an atomizer for stage (f).

The dried silicas obtained in conclusion of stage (f) can optionally be subjected to a stage of agglomeration, in particular by direct compression, by wet granulation (that is to say, with use of a binder, such as water), by extrusion and, preferably, by dry compacting. When the latter technique is employed, it can prove to be advantageous, before carrying out the compacting, to deaerate (operation also referred to as predensifying or degassing) the pulverulent products so as to remove the air included in the latter and to provide more uniform compacting. On conclusion of the agglomeration stage, the products can be graded to a desired size, for example by sieving. The compacted precipitated silica capable of being obtained is then advantageously provided in the form of granules. If appropriate, these granules can be provided in the most diverse shapes. The shapes which may be especially mentioned by way of example are spherical, cylindrical, parallelepipedal, tablet, flake, pellet and extrudate of circular or polylobar section. The mean dimensions of these granules are preferably between 2 and 20 mm.

The silica obtained on conclusion of stage (f) and then optionally agglomerated preferably exhibits a mean particle size or a median particle diameter of between 30 µm and 20 mm.

The silica obtained on conclusion of stage (f) and then optionally agglomerated can subsequently be micronized or, preferably, milled.

The silica then obtained preferably exhibits a mean particle size or a median particle diameter of less than 30 µm, preferably of less than 20 µm, in particular of between 5 and 15 µm, especially between 8 and 13 µm.

Micronizing can be carried out with a micronizer, such as an air jet mill.

Milling can be carried out in particular using a mechanical mill, for example of the ACM, Forplex, type, in particular a classifier hammer mill.

The precipitated silicas according to the present invention exhibit a very good aptitude for dispersing. They are particularly suitable, advantageously when they exhibit a mean particle size or a median particle diameter of less than 30 µm, preferably of less than 20 µm, in particular of between 5 and 15 µm, for example between 8 and 13 µm (silicas according to the first alternative form of the invention), for use as reinforcing filler in matrices based on elastomer(s), in particular clear or semi-clear elastomer(s), for shoe soles, as reinforcing filler in matrices based on silicone(s), in particular high temperature or room temperature vulcanizable silicone elastomer matrices, on which they confer good rheology properties, while providing them with highly satisfactory mechanical properties.

The silicas according to the invention have a particular advantageous application in the reinforcing of matrices based on elastomers, in particular clear or semi-clear elastomers, intended for the manufacture of shoe soles; these dispersible silicas make it possible for strong reinforcing of the transparent or translucent matrices used for the preparation of components made of transparent or translucent rubber which are constituents of shoe soles. Advantageously, they make it possible to obtain reinforced matrices having very good transparency.

The amount of silica according to the invention which can be used in this type of matrix is generally between 10 and 50%, in particular between 20 and 40%, with respect to the weight of the elastomer(s).

The silicas according to the invention have an equally advantageous application in the reinforcing of high temperature vulcanizable pasty or elastomeric organosilicon compositions (matrices) (HTV silicones, for example) or room temperature vulcanizable pasty or elastomeric organosilicon compositions (matrices) intended in particular for an insulation role, in particular the coating of electric cables. Said silicone-based matrices, in particular those intended for an insulation role, can be formed by extrusion, before being crosslinked. The low value for water uptake of the silicas of the invention makes it possible to avoid or to limit the formation of bubbles, in particular during the extrusion. These silica-based matrices can also be formed by molding. The silicas according to the invention advantageously confer, on the silicone matrices, very good electrical and mechanical properties, in particular with regard to tear strength or ultimate strength.

The nature of the vulcanizable organopolysiloxane or organopolysiloxanes present in this type of composition and that of the vulcanizing agents and other additives optionally present, as well as the vulcanizing conditions, are well known to a person skilled in the art; they are disclosed in particular in application WO 03/055801.

The amount of silica according to the invention which can be employed for the reinforcing of said matrices based on silicones can range from 3 to 20% when silicone pastes are concerned or from 5 to 50%, preferably from 10 to 40%, when a composition of elastomeric nature is concerned.

A possible application of the silicas according to the invention lies in their use as carrier for liquids, in particular due to their good absorption capacity and a highly satisfactory flowability.

Mention may be made, as liquids, of organic liquids, such as organic acids, surface-active agents, for example of anionic or nonionic type, organic additives for rubber/polymers, or pesticides.

Preferably, use is made here, as liquids, in particular of liquid additives, such as flavorings, colorants, liquid food supplements (in particular for the feeding of animals (for example vitamin E, vitamin E acetate or choline hydrochloride)) or preservatives, preferably carboxylic acids (propionic acid, for example).

The conditioned compositions comprising at least one liquid absorbed on a carrier formed by a silica according to the invention preferably exhibit a liquid content of at least 50% by weight, in particular of between 50 and 75% by weight, for example between 50 and 65% by weight.

Furthermore, the silicas of the invention can be employed as filler and/or carrier and/or excipient in various compositions, such as food, cosmetic or pharmaceutical compositions or compositions for the manufacture of paints or paper.

Mention may also be made of the use, for example in an amount of the order of 60% by weight, of the silica of the invention as carrier for solvent and/or for oil in compositions based on polymers intended for the preparation of separating porous membranes for batteries (battery separator); the solvent and/or the oil carried, once extracted after extrusion/calendaring, give rise to a network of pores.

The silica according to the invention, advantageously when it exhibits a mean particle size or a median particle diameter of between 30 μm and 20 mm (silica according to the second alternative form of the invention), can be incorporated in dentifrice compositions during the preparation of said compositions, which can be provided in the paste or gel form, and can thus make it possible to thicken these compositions or to provide them with the texture.

According to the invention, said silica can be used as thickening or texturing agent in a proportion of 0.1 to 20%, preferably of 0.5 to 15%, very particularly of 1 to 10%, by weight of the dentifrice composition.

Said dentifrice composition can additionally comprise other normal ingredients, in particular water-insoluble inorganic abrasive agents, optionally other thickening agents, humectants, and the like.

Mention may in particular be made, as abrasive agents, of abrasive silicas, calcium carbonate, hydrated alumina, bentonite, aluminum silicate, zirconium silicate or sodium, potassium, calcium and magnesium metaphosphates and phosphates. The total amount of abrasive powder(s) can constitute of the order of 5 to 50% of the weight of the dental composition.

Mention may be made, among the other thickening agents, of xanthan gum, guar gum, carrageenans, cellulose derivatives, alginates, in an amount which can range up to 5% of the weight of said composition, and the like.

Mention may be made, among the humectant agents, for example, of glycerol, sorbitol, polyethylene glycols, polypropylene glycols or xylitol, in an amount of the order of 2 to 85%, preferably of the order of 3 to 55%, of the weight of dentifrice composition, expressed on a dry basis.

In addition, these compositions can comprise in particular surface-active agents, detergent agents, colorants, antibacterials, fluorinated derivatives, opacifiers, flavorings, sweeteners, agents for combating tartar or plaque, bleaching agents, sodium bicarbonate, antiseptics, enzymes or natural extracts (camomile, thyme, and the like).

The following examples illustrate the invention without, however, limiting the scope thereof.

EXAMPLES 1-3

Model Opaque Toothpaste

| | |
|---|---|
| sorbitol (Neosorb 70/70 (Roquette Fréres)) | 45 |
| polyethylene glycol PEG 1500 | 5 |
| sodium saccharinate | 0.2 |
| sodium fluoride | 0.08 |
| sodium monofluorophosphate | 0.72 |
| water | 24.2 |
| abrasive silica (Tixosil 63, sold by Rhodia) | 10 |
| silica of the invention | 7 |
| titanium dioxide | 1 |
| spearmint flavoring | 1 |
| foaming agent (30% in water): Texapon Z 95 P (Cognis) | 5 |

Measurement of the Viscosity of a Dentifrice Formulation

The viscosity is determined on a tube of paste with a diameter of 25 mm at predetermined periods at 37° C. after preparation of the paste.

The measurement equipment used is a Brookfield RVT viscometer equipped with a Helipath device. The TE spindle is used at 5 rpm (revolutions per minute). The measurement is carried out in a downward direction after 90 seconds.

Example 1

14 000 g of water and 450 g of a 236 g/l (as $SiO_2$ equivalent) aqueous sodium silicate solution were introduced into a reactor equipped with a system for regulating the temperature and pH and with a system for stirring with a 3-bladed propeller, the $SiO_2/Na_2O$ ratio by weight (Rw) of the sodium silicate used being 3.46.

After starting to stir (250 revolutions per minute), the vessel heel thus formed was heated to 95° C. and the pH was brought to 7.5, over 11 minutes, by addition of an 80 g/l aqueous sulfuric acid solution (mean flow rate of 61 g per minute).

Once the pH of 7.5 was reached, 3045 g of a 236 g/l (as $SiO_2$ equivalent) aqueous sodium silicate solution (Rw=3.46) were added continuously at a constant flow rate of 35 grams per minute (duration of addition: 87 minutes) while maintaining the pH of the medium at a value equal to 7.5 (to within about 0.1 pH unit) by addition to the medium of an 80 g/l aqueous sulfuric acid solution with a flow rate controlled according to the change measured for the pH of the medium. Taking stock, 3383 g of the sulfuric acid solution were added to the medium, which corresponds to a mean flow rate of 40 grams of sulfuric acid solution added per minute.

After the period of addition of 87 minutes, the addition of silicate was halted and addition of acid was continued until the pH of the reaction mixture had stabilized at 3.6. Maturing was carried out by leaving the solution to stir for 5 minutes.

The slurry obtained was subsequently filtered and washed on a flat filter and then the cake obtained, the loss on ignition of which is 80.5%, was disintegrated mechanically at a pH of 5.5 and was then dried by rotary atomization.

The physicochemical characteristics of the unmilled dry silica obtained are as follows:
pH: 5.9
median particle diameter: 80 μm
median diameter after ultrasound: 31.0 μm
% greater than 51 μm after ultrasound: 18.6
$Na_2SO_4$ content: 1.6% by weight (with respect to the total weight of the material in the dry state)
CTAB specific surface: 133 $m^2/g$
BET specific surface: 143 $m^2/g$
DOP oil uptake: 305 ml/100 g
loss on ignition at 1000° C.: 6.5%
residual water content after 2 hours at 105° C.: 3.9%
water uptake: 5.8%
transmission: 80% at a refractive index of 1.460
packing density (PD): 0.27 g/ml
viscosity of the model toothpaste after 4 weeks: 250 mPa·s Example 2

The operations described in comparative example 1 are repeated, the dried product being milled so as to obtain a median particle diameter of 10 μm.

The physicochemical characteristics of the milled dry silica obtained are as follows:
pH: 5.9
median particle diameter: 10 μm
median diameter after ultrasound: 7 μm
% greater than 51 μm after ultrasound: 1.0
$Na_2SO_4$ content: 1.6% by weight (with respect to the total weight of the material in the dry state)
CTAB specific surface: 133 $m^2/g$
BET specific surface: 143 $m^2/g$
DOP oil uptake: 315 ml/100 g
loss on ignition at 1000° C.: 7%
residual water content after 2 hours at 105° C.: 4.4%
water uptake: 5.9%
transmission: 80% at a refractive index of 1.460
packing density (PD): 0.1 g/ml
viscosity of the model toothpaste after 4 weeks: 325 mPa·s Example 3

14 000 g of water and 630 g of a 236 g/l (as $SiO_2$ equivalent) aqueous sodium silicate solution were introduced into a reactor equipped with a system for regulating the temperature and pH and with a system for stirring with a 3-bladed propeller, the $SiO_2/Na_2O$ ratio by weight (Rw) of the sodium silicate used being 3.46.

After starting to stir (250 revolutions per minute), the vessel heel thus formed was heated to 95° C. and the pH was brought to 7.5, over 11 minutes, by addition of an 80 g/l aqueous sulfuric acid solution (mean flow rate of 61 g per minute).

Once the pH of 7.5 was reached, 3600 g of a 236 g/l (as $SiO_2$ equivalent) aqueous sodium silicate solution (Rw=3.46) were added continuously at a constant flow rate of 48 grams per minute (duration of addition: 75 minutes) while maintaining the pH of the medium at a value equal to 7.5 (to within about 0.1 pH unit) by addition to the medium of an 80 g/l aqueous sulfuric acid solution with a flow rate controlled according to the change measured for the pH of the medium. Taking stock, 3975 g of the sulfuric acid solution were added to the medium, which corresponds to a mean flow rate of 53 grams of sulfuric acid solution added per minute.

After the period of addition of 90 minutes, the addition of silicate was halted and addition of acid was continued until the pH of the reaction mixture had stabilized at 3.4. Maturing was carried out by leaving the solution to stir for 5 minutes.

The slurry obtained was subsequently filtered and washed on a flat filter and then the cake obtained, the loss on ignition of which is 86%, was disintegrated mechanically at a pH of 5 and was then dried by rotary atomization.

The physicochemical characteristics of the unmilled dry silica obtained are as follows:
pH: 5.3
median particle diameter: 65 μm
median diameter after ultrasound: 22 μm
% greater than 51 μm after ultrasound: 3.3
$Na_2SO_4$ content: 1.0% by weight (with respect to the total weight of the material in the dry state)
CTAB specific surface: 182 $m^2/g$
BET specific surface: 185 $m^2/g$
DOP oil uptake: 340 ml/100 g
loss on ignition at 1000° C.: 6.5%
residual water content after 2 hours at 105° C.: 3.9%
water uptake: 5.7%
transmission: 85% at a refractive index of 1.460
packing density (PD): 0.18 g/ml
viscosity of the model toothpaste after 4 weeks: 615 mPa·s Example 4

14 000 g of water and 450 g of a 236 g/l (as $SiO_2$ equivalent) aqueous sodium silicate solution were introduced into a reactor equipped with a system for regulating the temperature and pH and with a system for stirring with a 3-bladed propeller, the $SiO_2/Na_2O$ ratio by weight (Rw) of the sodium silicate used being 3.46.

After starting to stir (250 revolutions per minute), the vessel heel thus formed was heated to 98° C. and the pH was brought to 7.5, over 11 minutes, by addition of an 80 g/l aqueous sulfuric acid solution (mean flow rate of 61 g per minute).

Once the pH of 7.5 was reached, 3150 g of a 236 g/l (as $SiO_2$ equivalent) aqueous sodium silicate solution (Rw=3.46) were added continuously at a constant flow rate of 35 grams per minute (duration of addition: 90 minutes) while maintaining the pH of the medium at a value equal to 7.5 (to within about 0.1 pH unit) by addition to the medium of an 80 g/l aqueous sulfuric acid solution with a flow rate controlled according to the change measured for the pH of the medium. Taking stock, 3510 g of the sulfuric acid solution were added to the medium, which corresponds to a mean flow rate of 39 grams of sulfuric acid solution added per minute.

After the period of addition of 90 minutes, the addition of silicate was halted and addition of acid was continued until the pH of the reaction mixture had stabilized at 3.4. Maturing was carried out by leaving the solution to stir for 5 minutes.

The slurry obtained was subsequently filtered and washed on a flat filter and then the cake obtained, the loss on ignition of which is 86.4%, was disintegrated mechanically at a pH of 4.3 and was then dried by rotary atomization.

The dried silica was subsequently milled using a classifier hammer mill.

The physicochemical characteristics of the silica in the powder form obtained are as follows:

pH: 4.6
mean particle size: 12 μm
$Na_2SO_4$ content: 0.25% by weight (with respect to the total weight of the material in the dry state)
CTAB specific surface: 166 $m^2/g$
BET specific surface: 170 $m^2/g$
DOP oil uptake: 365 ml/100 g
loss on ignition at 1000° C.: 5%
residual water content after 2 hours at 105° C.: 2.5%
ater uptake: 5.8%
packing density (PD): 0.08 g/ml

The invention claimed is:

1. A precipitated silica comprising:
a CTAB specific surface of 140 to 230 $m^2/g$,
a DOP oil uptake of greater than 300 ml/100 g,
a water uptake of less than 6%,
a pH of 3.5 to 7.5,
a level of residual anion, expressed as sodium sulfate, of less than or equal to 2%, and
a mean particle size or a median particle diameter of less than 30 μm.

2. A precipitated silica according to claim 1, exhibiting:
a CTAB specific surface of 145 to 185 $m^2/g$,
a DOP oil uptake of 315 to 450 ml/100 g,
a water uptake of less than 6% and greater than 3%,
a pH of 4 to 7, and
a level of residual anion, expressed as sodium sulfate, of less than or equal 1.5%.

3. A precipitated silica according to claim 2 exhibiting:
a CTAB specific surface of 150 to 185 $m^2/g$,
a DOP oil uptake of greater than 320 to 400 ml/100 g,
a water uptake of greater than or equal to 4% and less than or equal to 5.8%,
a pH of 4 to 6, and
a level of residual anion, expressed as sodium sulfate, of less than or equal to 1%.

4. A precipitated silica according to claim 3, exhibiting:
a CTAB specific surface of 150 to 180 $m^2/g$,
a DOP oil uptake of 340 to 380 ml/100 g, and
a level of residual anion, expressed as sodium sulfate, of less than or equal to 0.5%.

5. The silica as claimed in claim 1, wherein the mean particle size or a median particle diameter is less than 20 μm.

6. The silica as claimed in claim 1, having a median particle diameter, after deagglomeration under ultrasound, of at most 35 μm.

7. The silica as claimed in claim 1, having a BET specific surface such that the BET-CTAB difference is at most 30 $m^2/g$.

8. The silica as claimed in claim 1, having a packing density of at most 0.3 g/ml.

9. The silica as claimed in claim 1, in the form of a powder.

10. A process for the preparation of a silica as claimed in claim 1, comprising the following stages:

(a) producing a starting vessel heel with a temperature of between 80 and 100° C., comprising water and a silicate, with a concentration of silicate in said vessel heel, expressed as $SiO_2$ equivalent, being less than or equal to 15 g/l;

(b) adding, at a temperature of between 80 and 100° C., an acidifying agent to bring the pH of the medium to a value of between 7 and 8, to form a medium;

(c) in the medium thus produced in stage (b), carrying out, at a temperature of between 80 and 100° C., a simultaneous addition of a silicate and of an acidifying agent, with a respective amounts of silicate and of acidifying agent added over time being specifically chosen so that, throughout the duration of the addition:
the pH of the reaction medium remains between 7 and 8 and optionally between 7.2 and 7.8; and
the concentration of silicon in the medium, expressed as $SiO_2$ equivalent, remains less than or equal to 35 g/l;

(d) adding, at a temperature of between 80 and 100° C., an acidifying agent to the medium obtained on conclusion of stage (c) so as to bring the medium to a pH of between 3 and 6.5 to obtain an aqueous silica dispersion;

(e) filtering the aqueous silica dispersion obtained in stage (d) in order to obtain a filtration cake;

(f) drying the filtration cake produced on conclusion of the stage (e), optionally washing it beforehand; and (g) optionally milling or micronizing the silica obtained on conclusion of stage (f);

wherein as a result of the process the filtration cake exhibits, prior to the drying of it in stage (f), a loss on ignition at 1000° C. of greater than 82%.

11. Shoe soles comprising the silica as defined in claim 1.

12. A matrix based on silicone(s) comprising the silica as defined in claim 1 as reinforcing filler.

13. A carrier for liquids comprising the silica as defined in claim 1.

14. A dentifrice composition in the paste or gel form comprising the silica as defined in claim 1 as a thickening agent.

15. Battery separators comprising the silica as defined in claim 1.

16. The precipitated silica according to claim 1, wherein the water uptake is greater than 3%.

17. The precipitated silica according to claim 5, wherein the mean particle size or median particle diameter is 5 to 15 μm.

18. The precipitated silica according to claim 17, wherein the mean particle size or median particle diameter is 8 to 13 μm.

19. The precipitated silica according to claim 6, wherein the median particle diameter, after deagglomeration under ultrasound, is at most 25 μm.

20. The precipitated silica according to claim 7, wherein the BET-CTAB difference is at most 10 $m^2/g$.

21. The precipitated silica according to claim 8, wherein the packing density is 0.04 to 0.3 g/ml.

22. The precipitated silica according to claim 10, wherein the temperature in stage (a) is greater than or equal to 90° C.

23. The precipitated silica according to claim 10, wherein the temperature in stage (b) is 90 to 100° C.

24. The precipitated silica according to claim 10, wherein the pH in stage (b) is 7.3 to 7.7.

25. The precipitated silica according to claim 10, wherein the temperature in stage (c) is 90 to 100° C.

26. The precipitated silica according to claim 10, wherein the temperature in stage (d) is 90 to 100° C.

27. The precipitated silica according to claim 10, wherein the loss on ignition and 1000° C. is 84 to 88%.

28. The precipitated silica according to claim 1, wherein the DOP oil uptake is greater than 310 ml/100 g.

29. The precipitated silica according to claim 10, wherein the loss on ignition and 1000° C. is greater than 84%.

30. A precipitated silica comprising:
a CTAB specific surface of 140 to 230 m²/g,
a DOP oil uptake of greater than 300 ml/100 g,
a water uptake of less than 6%,
a pH of 3.5 to 7.5,
a level of residual anion, expressed as sodium sulfate, of less than or equal to 2%, and
a mean particle size or a median particle diameter of between 30 μm and 20 mm.

* * * * *

UNITED STATES PATENT AND TRADEMARK OFFICE
CERTIFICATE OF CORRECTION

PATENT NO. : 7,799,304 B2  Page 1 of 1
APPLICATION NO. : 10/583417
DATED : September 21, 2010
INVENTOR(S) : Adrien Dromard et al.

It is certified that error appears in the above-identified patent and that said Letters Patent is hereby corrected as shown below:

On the Title Page, Item (30) Foreign Application Priority Data: change "Dec. 19, 2003" to --Dec. 19, 2004--.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,799,304 B2 | Page 1 of 1 |
| APPLICATION NO. | : 10/583417 | |
| DATED | : September 21, 2010 | |
| INVENTOR(S) | : Adrien Dromard et al. | |

It is certified that error appears in the above-identified patent and that said Letters Patent is hereby corrected as shown below:

Title page, Item (30) Foreign Application Priority Data "Dec. 19, 2004" (as substituted by Certificate of Correction issued November 30, 2010) is to be reinstated to read --December 19, 2003--.

Signed and Sealed this
Twenty-fifth Day of January, 2011

David J. Kappos
*Director of the United States Patent and Trademark Office*